:::
United States Patent [19]

Schwarzer et al.

[11] 3,937,612

[45] Feb. 10, 1976

[54] DIALKYLPHOSPHONOACETYLUREA COMPOUNDS AND PROCESSES FOR PREPARATION AND USE FOR FLAMEPROOFING

[75] Inventors: Johann Schwarzer, Augsburg; Peter Meins, Haan Rhineland; Kurt Voparil, Leverkusen, all of Germany

[73] Assignee: Henkel & Cie GmbH, Dusseldorf-Holthausen, Germany

[22] Filed: Dec. 26, 1974

[21] Appl. No.: 536,305

[30] Foreign Application Priority Data
Jan. 5, 1974 Germany............................ 2400393

[52] U.S. Cl.............................. 8/186; 8/116 P; 8/183; 8/185; 260/251 P; 260/309.7; 260/849; 260/856; 260/938; 427/381; 427/382; 428/276; 428/921
[51] Int. Cl.²........................................ D06M 13/28
[58] Field of Search............ 260/251 P, 938, 309.7; 8/116 P, 182, 183, 187, 186; 427/381, 382; 428/276

[56] References Cited
UNITED STATES PATENTS

| | | | |
|---|---|---|---|
| 2,494,126 | 1/1950 | Hoegberg........................... | 260/938 |
| 3,629,280 | 12/1971 | Newallis........................... | 260/251 P |
| 3,679,778 | 7/1972 | Nachbur et al.................... | 260/938 |
| 3,725,272 | 4/1973 | Petersen et al.................... | 8/183 |
| 3,754,859 | 8/1973 | Doerr................................. | 8/182 |
| 3,763,281 | 10/1973 | Weil................................... | 260/938 |
| 3,763,283 | 10/1973 | Curgan .............................. | 260/938 |

Primary Examiner—Murray Tillman
Assistant Examiner—A. H. Koeckert
Attorney, Agent, or Firm—Hammond & Littell

[57] ABSTRACT

Dialkylphosphonoacetylurea compounds which contain hydroxymethyl groups or alkoxymethyl groups and their preparation, as well as their use for the flameproofing of cellulose-containing materials.

8 Claims, No Drawings

DIALKYLPHOSPHONOACETYLUREA COMPOUNDS AND PROCESSES FOR PREPARATION AND USE FOR FLAMEPROOFING

OBJECTS OF THE INVENTION

It is an object of the present invention to provide new dialkylphosphonoacetylurea compounds which contain hydroxymethyl groups or alkoxymethyl groups, as well as a process for the preparation thereof.

It is another object of the present invention to provide a process for the use of new dialkylphosphonoacetylurea compounds containing hydroxymethyl groups or alkoxymethyl groups, for the flameproofing of cellulose-containing materials.

These and other objects of the present invention will become apparent as the description thereof proceeds.

DESCRIPTION OF THE INVENTION

The present invention is directed to new dialkylphosphonoacetylurea compounds which contain hydroxymethyl groups or alkoxymethyl groups, and the process of preparing these compounds, as well as the use thereof for the flameproofing of cellulose-containing materials.

The new compounds of the present invention have the formula I

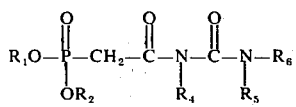

in which $R_1$ and $R_2$ are identical alkyl having 1 to 4 carbon atoms; $R_4$, $R_5$ and $R_6$ are either alkyl having 1 to 4 carbon atoms, hydroxymethyl, or alkoxymethyl having 1 to 4 carbon atoms in the alkoxy, whereby at least one of $R_4$, $R_5$ and $R_6$ is said hydroxymethyl or said alkoxymethyl; and wherein $R_4$ and $R_5$ can also jointly form a hydrocarbon chain having two or three carbon atoms, such as the ethylene or propylene radical.

More particularly, the present invention provides a compound having the formula

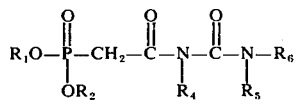

wherein $R_1$ and $R_2$ are each the same alkyl having 1 to 4 carbon atoms, $R_4$, $R_5$ and $R_6$ are each selected from the group consisting of alkyl having 1 to 4 carbon atoms, hydroxymethyl and alkoxymethyl having 2 to 5 carbon atoms, with the proviso that at least one of $R_4$, $R_5$ and $R_6$ is selected from the group consisting of hydroxymethyl and alkoxymethyl having 2 to 5 carbon atoms, and wherein $R_4$ and $R_5$ can together form an alkylene chain having 2 to 3 carbon atoms.

A particularly preferred subgenus of the compounds according to the invention are those wherein $R_1$ and $R_2$ are each the same alkyl having 1 to 2 carbon atoms, $R_4$, $R_5$ and $R_6$ are each selected from the group consisting of hydroxymethyl and alkoxymethyl having 2 to 3 carbon atoms, and with the proviso that at least one of $R_4$, $R_5$ and $R_6$ is selected from the group consisting of hydroxymethyl and alkoxymethyl having 2 to 3 carbon atoms, and wherein $R_4$ and $R_5$ can together form an alkylene chain having 2 to 3 carbon atoms.

The manufacture of the compounds according to the invention is characterized in that a chloroacetylurea compound having the formula II

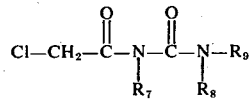

in which $R_7$, $R_8$ and $R_9$ designate either hydrogen or alkyl having 1 to 4 carbon atoms, whereby at least one of $R_7$, $R_8$ and $R_9$ is hydrogen, and whereby the $R_7$ and $R_8$ can also jointly form a hydrocarbon chain with 2 or 3 carbon atoms, are condensed with trialkyl phosphite having the formula III

in which $R_1$, $R_2$ and $R_3$ designate identical alkyl having 1 to 4 carbon atoms; and characterized in that the product thus produced is caused to react with formaldehyde in neutral or alkaline solution and, if necessary, is etherified with an alcohol having 1 to 4 carbon atoms in the presence of an acid.

More particularly, the present invention is directed to a process for the preparation of a hydroxymethylated dialkylphosphonoacetylurea of the formula

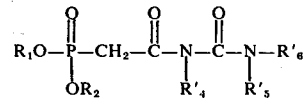

wherein $R_1$ and $R_2$ are each the same alkyl having 1 to 4 carbon atoms, $R'_4$, $R'_5$ and $R'_6$ are selected from the group consisting of alkyl having 1 to 4 carbon atoms and hydroxymethyl, with the proviso that at least one of $R'_4$, $R'_5$ and $R'_6$ is hydroxymethyl, and wherein $R_4$ and $R_5$ can together form an alkylene chain having 2 to 3 carbon atoms, comprising reacting a chloroacetylurea compound of the formula

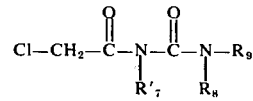

wherein $R_7$, $R_8$ and $R_9$ are each selected from the group consisting of hydrogen and alkyl having 1 to 4 carbon atoms, with the proviso that at least one of $R_7$, $R_8$ and $R_9$ is hydrogen, and wherein $R_7$ and $R_8$ can together form an alkylene chain having 2 to 3 carbon atoms, with a trialkylphosphite of the formula

wherein $R_1$, $R_2$, and $R_3$ are each the same alkyl having 1 to 4 carbon atoms, at a temperature between 100°C to 170°C,
continuously removing the alkyl chloride which is formed by the reaction,
reacting the resultant dialkylphosphonoacetylurea with a reactant selected from the group consisting of an aqueous formaldehyde solution at a pH of at least 7.0, and paraformaldehyde in the presence of an alkaline reacting substance,
and recovering said hydroxymethylated dialkylphosphonoacetylurea.

In addition the present invention is furthermore directed to a process for the preparation of an alkoxymethylated dialkylphosphonoacetylurea of the formula

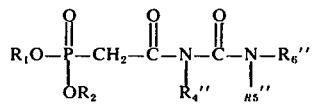

wherein $R_1$ and $R_2$ are each the same alkyl having 1 to 4 carbon atoms,
$R''_4$, $R''_5$ and $R''_6$ are each selected from the group consisting of alkyl having 1 to 4 carbon atoms, hydroxymethyl and alkoxymethyl having 2 to 5 carbon atoms,
with the proviso that at least one of $R''_4$, $R''_5$ and $R''_6$ is alkoxymethyl having 2 to 5 carbon atoms,
comprising reacting the hydroxymethylated dialkylphosphonoacetylurea produced by the above process, in the presence of an acid at a pH less than 7, with an alkanol having 1 to 4 carbon atoms, and
recovering said alkoxymethylated dialkylphosphonoacetylurea.

The chloroacetylurea compounds having the formula II which are used as starting materials are representatives of a known class of materials. They can be prepared according to known methods, for example, from correspondingly substituted ureas and chloroacetyl chloride. For the manufacture of the dialkylphosphonoacetylureas according to the invention, several compounds are suitable, among which are the compounds

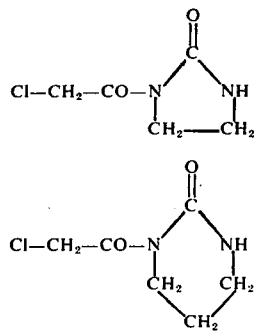

as well as compounds having the formula $Cl - CH_2 - CO - NR - CO - NR'R''$ wherein R, R' and R'' have the meanings listed in the following Table I

TABLE I

| R | R' | R'' |
|---|---|---|
| H | H | H |
| H | H | $CH_3$ |
| H | H | $C_2H_5$ |
| H | H | $N-C_3H_7$ |
| H | H | iso-$C_3H_7$ |
| H | H | n-$C_4H_9$ |
| H | H | sec-$C_4H_9$ |
| H | $CH_3$ | $CH_3$ |
| H | $C_2H_5$ | $C_2H_5$ |
| H | n-$C_3H_7$ | n-$C_3H_7$ |
| H | n-$C_4H_9$ | n-$C_4H_9$ |
| $CH_3$ | H | $CH_3$ |
| $C_2H_5$ | H | $C_2H_5$ |
| n-$C_3H_7$ | H | n-$C_3H_7$ |
| iso-$C_3H_7$ | H | iso-$C_3H_7$ |
| n-$C_4H_9$ | H | n-$C_4H_9$ |
| sec-$C_4H_9$ | H | sec-$C_4H_9$ |
| $CH_3$ | H | $C_2H_5$ |
| $CH_3$ | H | n-$C_4H_9$ |
| $C_2H_5$ | H | H |

Suitable examples of trialkyl phosphites having the formula III are the following compounds: Trimethyl phosphite, triethyl phosphite, tri-n-propyl phosphite, tri-iso-propyl phosphite, tri-n-butyl phosphite, and tri-sec-butyl phosphite.

For the preparation of the dialkylphosphonoacetylurea compounds, the trialkyl phosphite and the chloroacetylurea derivative are reacted with each other, at a temperature between 100°C to 170°C, preferably at temperatures of about 140°C to 170°C. When trimethyl phosphite is used, it is necessary to maintain the reaction temperature at about 100°C up to 112°C, since this ester boils at 112°C. Preferably, the trialkyl phosphite is charged first, and the chloroacetylurea compound is added gradually. The alkyl chloride which is formed by the reaction has to be continuously removed, such as by being distilled from the reaction mixture. In general, the reactants are allowed to react as such; however, it is also possible to carry out the reaction in an inert organic solvent which does not react with the starting materials or the reaction product. Suitable inert organic solvents are, for example, xylene and dibutyl ether. After the reaction has been completed, non-converted trialkyl phosphite which is potentially present, as well as a solvent which is optionally used, are distilled off from the reaction mixture, advantageously under vacuum. Then, the desired dialkylphosphonoacetylurea remains as a residue. Some of the compounds prepared in this manner are crystallizing substances, whereas the others are viscous liquids. These products can be purified by recrystallization or reprecipitation from suitable solvents, for example lower alkanols such as isopropanol or lower alkanones such as acetone.

For the preparation of the hydroxymethylated dialkylphosphonoacetylureas according to the invention, the above described dialkylphosphonoacetylurea compounds are reacted with an aqueous formaldehyde solution. The pH-value of the reaction mixture is adjusted to at least 7.0 or above 7.0 by the addition of a base, such as an alkali metal hydroxide, for example sodium hydroxide or potassium hydroxide. It is preferable during the reaction that the temperature of the reaction mixture be maintained within the range of 40°C to 60°C. In certain cases, the reaction product does not need to be isolated, but can be used directly in form of the aqueous solution obtained, for the preparation of liquors destined for the flameproofing of cellulose-containing materials.

For carrying out the hydroxymethylation, it is also possible to heat the dialkylphosphonoacetylurea compound with paraformaldehyde in the presence of an alkaline reacting substance, for example an alkali metal carbonate such as sodium carbonate or potassium carbonate, or an alkali metal hydride such as sodium hydride at a temperature of 75°C to 150°C. Alternatively, the reaction can be allowed to proceed in the presence of an inert organic solvent, such as ethanol, isopropanol, dioxane, or tetrahydrofuran, advantageously in a refluxing operation. This method is preferred when the hydroxymethylated dialkylphosphonoacetylurea compounds are to be prepared as such. When the reaction is carried out in the absence of a solvent, the desired compound is obtained directly; otherwise, it is obtained as a residue after the solvent has been distilled off.

For the preparation of the alkoxymethylated dialkylphosphonoacetylurea compounds, the above-described hydroxymethylated dialkylphosphonoacetylurea compounds, in the presence of an acid at a pH less than 7, preferably pH4 to 6 are reacted with a monohydric aliphatic alcohol having 1 to 4 carbon atoms, preferably an alkanol having 1 to 4 carbon atoms. Preferably the hydroxymethyl derivative is dissolved in an excess of the respective alcohol; then the acid is added and the mixture is refluxed until the etherification reaction is completed. For the adjustment to an acidic pH-value, it is recommended to use a solution of hydrogen chloride in the alcohol chosen for the etherification.

The material to be flameproofed is usually a textile consisting wholly or substantially of cellulose or regenerated cellulose fibers. Aqueous solutions containing flameproofing ingredients are prepared, and usually contain from 20% to 50% by weight, preferably 30% to 40% by weight, of the compounds of the invention. This corresponds to 200 to 500 gm/liter, preferably 300 to 400 gm/liter of solution, of these compounds of the invention.

When the compounds having the formula I are to be used for the flameproofing of this cellulose-containing materials according to the invention, it is preferable to charge them mixed with aminoplasts. For this purpose, condensation products of melamine and formaldehyde or etherified melamineformaldehyde condensation products can be used, such as etherified polymethylolmelamine having about 5 methylol groups per molecule. Suitable also are condensation products of formaldehyde and urea or urea derivatives, such as for example, ethyleneurea or N, N'-diethylurea. Mixtures of these aminoplasts can also be used. The aqueous flameproofing solutions contain 1% to 20% by weight, preferably 5% to 8% by weight, of these aminoplasts. This corresponds to 10 to 200 gm/liter, preferably 50 to 80 gm/liter of solution, of these aminoplasts.

It has been found useful to add catalysts to such preparations to speed up the curing of the aminoplasts and their condensation with compounds having the formula I. For this purpose, all substances are suitable which are customarily used as inorganic catalysts for the curing of aminoplasts on cellulose-containing materials for example an ammonium halide such as ammonium chloride, ammonium dihydrogen phosphate, an alkaline earth metal halide such as magnesium chloride and zinc nitrate. These catalysts are present in the aqueous flameproofing solutions in the range of 0.1% to 1.0% by weight, preferably 0.4% to 0.6% by weight. This corresponds to 1 to 10 gm/liter, preferably 4 to 6 gm/liter of solution of these catalysts.

It is also useful optionally to add organic crosslinking agents to the aqueous flameproofing solutions such as alkylene polyamines having 2 to 5 carbon atoms such as ethylene diamine, or aliphatic amides having 1 to 5 carbon atoms such as urea. These organic cross-linking agents assist in the curing of the aminoplasts as well as in the condensing with compounds of the formula I. The organic cross-linking agents are present in the aqueous flameproofing solution in the range of 0% to 5.0% by weight, preferably 0.9% to 1.1% by weight. This corresponds to 0 to 50 gm/liter, preferably 9 to 11 gm/liter of solution, of the cross-linking agents.

The process for the flameproofing of cellulosecontaining material consists in impregnating the article with such a preparation, then, drying the article to evaporate the solvent present and finally, heating the treated article to cure the aminoplast and to condense it with the compounds having the formula I.

More particularly, the present invention provides a process for flameproofing a textile consisting wholly or substantially of cellulose or regenerated cellulose fibers comprising impregnating said textile with an effective amount of an aqueous flameproofing solution consisting essentially of a. from 20% to 50% by weight of a compound according to the invention,
b. from 1% to 20% by weight of an aminoplast and
c. from 0% to 5% by weight of a cross-linking agent,
d. from 0.1% to 1.0% by weight of a catalyst, and
e. the balance up to 100% by weight of water;

drying said impregnated textile to evaporate the solvent;

heating the dried textile to cure the said aminoplast and to condense said aminoplast with said compound according to the invention; and recovering said flameproof textile.

The following examples are merely illustrative of the present invention without being deemed limitative in any manner thereof.

EXAMPLE 1 a. Preparation of Diethylphosphonoacetylurea

While stirring, 682 gm (5 mol) of chloroacetylurea were added portionwise to 831 gm (5 mol) of triethyl phosphite at a temperature of 135°C to 150°C. Each time, the addition of the next portion was delayed until the violent gas evolution had abated. After the last portion of chloroacetylurea had been added, the stirring was continued at 150°C until the evolution of gas was terminated. Small quantities of a volatile substance distilled off when the reaction mixture was heated on the water bath under the vacuum generated by an oil pump. The reaction mixture solidified upon cooling. The pure diethylphosphonoacetylurea was obtained from the crude product by recrystallization from isopropanol or acetone and proved to be a water-soluble product having a melting point of 120°C. The yield of crude product was 1120 gm (94% of the theory).

Elemental Analysis for $C_7 H_{15} N_2 O_5 P$:
   Calc. (%) : 35.3 C 6.3 H 11.8 N 13.0 P
   Found (%) : 35.3 C 6.4 H 11.9 N 12.7 P
IR-Spectrum (KBr : $cm^{-1}$):
   3380 m, 3220 sh, 3170 m, 3100 sh, 2990 m, 2930 w,
   1718 s, 1697 s, 1604 m, 1515 w, 1400 m, 1310 s, -continued 1233 s, 1208 w, 1160 - 1100 w, 1050 s, 1020 s,
975 m, 950 m, 860 m, 820 m, 788 w,
$^1H$ - NMR-Spectrum (15% in $CDCl_3$ ; 60 MHz):

Position in ppm against int. TMS (tetramethylsilane) (relative intensity) splitting picture (coupling constants in $H_2$) — 1.33 (6), triplet (7) — 3.10 (2), doublet (22.5) – 4.18 (4), pseudoquintet with indication of further splittings;
(7 – 8) -- 6.65 (1), broad -- 7.95 (1), broad -- 9.90 (1). The signals at 6.65, 7.95 and 9.90 disappear during the $D_2O$-exchange.

b. Preparation of N-Diethylphosphonoacetyl-N′,N′-tris-(hydroxymethyl)-urea

500 Gm (2.1 mol) of diethylphosphonoacetylurea and 69 gm (2.3 mol) of paraformaldehyde were dissolved in 5 liters of absolute tetrahydrofuran, and after the addition of about 0.5 gm of sodium hydride, were refluxed for 1 hour. Subsequently, the solvent was distilled off under the vacuum generated by a water-jet pump. The remaining yellowish, viscous substance crystallized after standing from 3 to 4 days. The melting point was 177°C (sinters from about 100°C on). The determination of the total formaldehyde and the free formaldehyde gave a degree of hydroxymethylation amounting to about 100%.

The compound had the formula $$C_2H_5O-\overset{O}{\underset{OC_2H_5}{P}}-CH_2-\overset{O}{C}-N-\overset{O}{C}-N-CH_2OH$$
$$\phantom{C_2H_5O-\overset{O}{\underset{OC_2H_5}{P}}-CH_2-\overset{O}{C}-N} CH_2OH\ CH_2OH$$

c. Preparation of N-Diethylphosphonoacetyl-N′,N′-trisethoxymethyl-urea

200 Gm of N-diethylphosphonoacetyl-N,N′,N′-tris-(hydroxymethyl)-urea was dissolved in 400 ml of ethanol. The pH-value of the mixture was adjusted to about 2.5 by the addition of several milliliters of an ethanolic hydrochloric acid solution.

Next, the solution was refluxed for two hours. After neutralization with sodium carbonate, the solution was filtered, and the excess ethanol was distilled off. N-diethylphosphonoacetyl-N,N′,N′-tris-(ethoxymethyl)-urea remained as a yellowish, viscous liquid, and had the formula $$C_2H_5O-\overset{O}{\underset{OC_2H_5}{P}}-CH_2-\overset{O}{C}-N-\overset{O}{C}-N-CH_2OC_2H_5$$
$$\phantom{C_2H_5O-\overset{O}{\underset{OC_2H_5}{P}}-CH_2-\overset{O}{C}-N} CH_2OC_2H_5\ CH_2OC_2H_5$$

EXAMPLE 2 a. Preparation of 1-(Diethylphosphonoacetyl)-imidazolidin-2-one.

While stirring, 813 gm (5 mol) of 1-chloroacetyl-2-imidazolidinone were added to 831 gm (5 mol) of triethylphosphite at a temperature of 135°C to 150°C. After the addition had been completed, the reaction mixture was stirred at 150°C until gas evolution no longer could be detected. Then, traces of non-converted trialkyl phosphite were distilled off under vacuum. Recrystallization from isopropanol of the crude product thus obtained made it possible to obtain the pure product having a melting point of 100°C to 102°C. The yield of crude product amounted to 1250 gm (95% of theory).

Elemental Analysis for $C_9 H_{17} N_2 O_5 P$:
  Calcd. (%) : 40.9 C ; 6.5 H ; 10.6 N ; 11.7 P
  Found (%) : 40.7 C ; 6.4 H ; 10.4 N ; 11.3 P
IR-Spectrum (KBr; $cm^{-1}$):
  3250 s, 2990 m, 2940 m, 2910 m, 1760 s, 1730 s,
  1670 s, 1405 s, 1360 s, 1260 s, 1250 s, 1223 s,
  1126 m, 1070 m, 1045 s, 1020 s, 978 s, 964 s,
  956 s, 832 m, 788 m, 753 m, 675 m.
$^1H$ - NMR-Spectrum (15% in DMSO - $d^6$):

Position in ppm against TMS (relative intensity), splitting (coupling constants in Hz) — 1.25 (6), triplet (7) - 3.2 - 4.3 (10), a signal group having a complex structure — 7.73 (1), broad singlet. The signal at 7.73 (1) disappeared upon the addition of $D_2O$.

b. Preparation of 1 — (Diethylphosphonoacetyl)-3-hydroxymethyl-imidazolidin-2-one 264 Gm (1 mol) of 1-(Diethylphosphonoacetyl)-imidazolidin-2-one and 33 gm of paraformaldehyde (1.1 mol) were dissolved in 2.5 liters of tetrahydrofuran; and after the addition of about 0.3 gm of sodium hydride, the solution was refluxed for one hour. After the solvent had been distilled off, there remained 1-(diethylphosphonoacetyl)-3-hydroxymethylimidazolidin-2-one as a yellowish, viscous liquid. The determination of the total formaldehyde and the free formaldehyde gave a degree of hydroxymethylation amounting to 100%. The compound had the formula $$C_2H_5O-\overset{O}{\underset{OC_2H_5}{P}}-CH_2-\overset{O}{C}-N\underset{CH_2-CH_2}{\overset{\overset{O}{\|}}{\diagup C\diagdown}}N-CH_2OH$$

c. Preparation of 1-(Diethylphosphonoacetyl)-3-methoxymethylimidazolidin-2-one 100 Gm of 1-diethylphosphonoacetyl)-3-hydroxymethylimidazolidin-2-one was dissolved in 200 ml of methanol. The pH-value of the mixture was adjusted to about 3.0 by the addition of several of milliliters of a methanolic hydrochloric acid solution. Then, the mixture was refluxed for 1.5 hours. After neutralization with sodium carbonate, and filtration, the excess methanol was distilled off. 1-(Diethylphosphonoacetyl)-3-methoxymethyl-imidazolidin-2-one remained as a yellowish, viscous liquid, having the following formula $$C_2H_5O-\overset{O}{\underset{OC_2H_5}{P}}-CH_2-\overset{O}{C}-N\underset{CH_2-CH_2}{\overset{\overset{O}{\|}}{\diagup C\diagdown}}N-CH_2OCH_3$$

EXAMPLE 3

Aqueous liquors having the following composition were prepared from the following ingredients

SOLUTION 1

350 Gm/liter of N-diethylphosphonoacetyl-N,N',N'-tris-(hydroxymethyl)-urea prepared in Example 1 above;

80 Gm/liter of 90% aqueous solution of a commercially available etherified polymethylolmelamine having about 5 methylol groups per molecule;

10 gm/liter of urea and 5 gm/liter of ammonium chloride.

SOLUTION 2

350 Gm/liter of 1-(diethylphosphonoacetyl)-3-hydroxymethyl-imidazolidin-2-one prepared in Example 2 above;

80 gm/liter of 90% aqueous solution of a commercially available etherified polymethylolmelamine having about 5 methylol groups per molecule;

10 gm/liter of urea and 5 gm/liter of ammonium chloride.

Cotton fabrics for overcoats (190 gm/m²) were impregnated with these two solutions and uniformly squeezed out on the Foulard padding machine until the weight increase to amounted 60% to 100% preferably 80%; then the fabrics were dried at 100°C to 120°C preferably 110°C and finally exposed to a curing temperature of 160°C to 200°C preferably 180°C for 80 to 100 seconds preferably 90 seconds to cure the aminoplast material and to condense it with the compounds of the invention.

FLAMMABILITY TEST

The flammability was tested according to DIN 53,906 whereby the specimen was suspended in a vertical holder and subjected to a flame along the edge. The duration of the test was 6 seconds. ("DIN" is the abbreviation for "Deutsche Industrie Norn" which is a published series of standard German test procedures similar to ASTM. The results are reported in Table I.

TABLE I

| Specimen Treated with | Burning Time in sec | Glowing Time in sec | Tearing length in mm |
|---|---|---|---|
| Solution 1 | 0 | 0 | 90 |
| Solution 2 | 0 | 0 | 85 |
| Non-Treated | 30 | 45 | Infinite |

TEARING STRENGTH TEST

The tearing strength was tested according to DIN 53,875. The specimens were clamped in the weft-direction. The clamped length was 20 cm, the width tested was 5 cm, and the drawing-off rate was 100 mm/min. The test results are reported in Table II.

TABLE II

| Specimen Treated with | Tearing Strength in Kp | Elongation in mm | Loss of Tearing Strength % |
|---|---|---|---|
| Solution 1 | 59.6 | 17 | 10.6 |
| Solution 2 | 56.3 | 13 | 15.6 |
| Non-Treated | 66.7 | 17 | — |

TEST OF PERMANENCE

For proof of the permanence of the flameproofing effect, the cotton fabric treated with solution 2 was subjected to hot laundering in a domestic washing machine equipped with a centrifuge (AEG- LAVAMAT). The washing liquid used contained 3 gm/liter of a commercially available detergent for washing machines. The ratio of the washing liquid was 1 : 30, and the washing temperature was 95°C. After washing and drying, the flammability test gave practically the same values as before the washing: burning time was 0 sec.; glowing time was 0 sec.; and tearing length was 90 mm.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. A compound having the formula

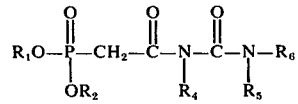

wherein $R_1$ and $R_2$ are each the same alkyl having 1 to 4 carbon atoms, $R_4$, $R_5$ and $R_6$ are each selected from the group consisting of alkyl having 1 to 4 carbon atoms, hydroxymethyl and alkoxymethyl having 2 to 5 carbon atoms, with the proviso that at least one of $R_4$, $R_5$ and $R_6$ is selected from the group consisting of hydroxymethyl and alkoxymethyl having 2 to 5 carbon atoms, and wherein $R_4$ and $R_5$ can together form an alkylene chain having 2 to 3 carbon atoms.

2. The compound of claim 1, which is N-diethylphosphonoacetyl-N,N',N'-tris-(hydroxymethyl)-urea.

3. The compound of claim 1, which is N-diethylphosphonoacetyl-N,N',N'-tris-(ethoxymethyl)-urea.

4. The compound of claim 1, which is 1-(diethylphosphonoacetyl)-3-hydroxymethyl-imidazolidin-2-one.

5. The compound of claim 1, which is 1-(diethylphosphonoacetyl)-3-methoxymethyl-imidazolidin-2-one.

6. The compound of claim 1, wherein $R_1$ and $R_2$ are each the same alkyl having 1 to 2 carbon atoms, $R_4$, $R_5$ and $R_6$ are each selected from the group consisting of hydroxymethyl and alkoxymethyl having 2 to 3 carbon atoms, and with the proviso that at least one of $R_4$. $R_5$ and $R_6$ is selected from the group consisting of hydroxymethyl and alkoxymethyl having 2 to 3 carbon atoms, and wherein $R_4$ and $R_5$ can together form an alkylene chain having 2 to 3 carbon atoms.

7. A process for flameproofing a textile consisting wholly or substantially of cellulose or regenerated cellulose fibers comprising impregnating said textile with an effective amount of an aqueous flameproofing solution consisting essentially of a. from 20% to 50% by weight of a compound according to claim 1,
b. from 1% to 20% by weight of a different aminoplast,
c. from 0% to 5% by weight of a cross-linking agent selected from the group consisting of alkylene polyamines having 2–5 carbon atoms and urea,
d. from 0.1% to 1.0% by weight of a catalyst, and
e. the balance up to 100% by weight of water;
   drying said impregnated textile to evaporate the solvent;
heating the dried textile to cure the said aminoplast and to condense said aminoplast with said compound according to claim 1; and
recovering said flameproof textile.

8. The process of claim 7, wherein said aqueous flameproofing solution consists essentially of
a. from 30% to 40% by weight of said compound according to claim 1,
b. from 5% to 8% by weight of said aminoplast,
c. from 0.9% to 1.1% by weight of said crosslinking agent,
d. from 0.4% to 0.6% by weight of said catalyst, and
e. the balance up to 100% by weight of water.

* * * * *